United States Patent
Plumptre

(10) Patent No.: US 9,144,649 B2
(45) Date of Patent: Sep. 29, 2015

(54) DOSE SETTING MECHANISM AND INJECTION DEVICE

(75) Inventor: David Aubrey Plumptre, Worcestershire (GB)

(73) Assignee: SANOFI-ADVENTIS DEUTSCHLAND GMBH, Frankfurt am Main (DE)

( * ) Notice: Subject to any disclaimer, the term of this patent is extended or adjusted under 35 U.S.C. 154(b) by 0 days.

(21) Appl. No.: 14/007,375

(22) PCT Filed: Mar. 22, 2012

(86) PCT No.: PCT/EP2012/055054
§ 371 (c)(1),
(2), (4) Date: Sep. 25, 2013

(87) PCT Pub. No.: WO2012/130703
PCT Pub. Date: Oct. 4, 2012

(65) Prior Publication Data
US 2014/0018745 A1    Jan. 16, 2014

(30) Foreign Application Priority Data
Mar. 25, 2011 (EP) ..................................... 11159756

(51) Int. Cl.
*A61M 5/315* (2006.01)
*A61M 5/24* (2006.01)

(52) U.S. Cl.
CPC .............. *A61M 5/31535* (2013.01); *A61M 5/24* (2013.01); *A61M 5/3155* (2013.01); *A61M 5/31525* (2013.01); *A61M 5/31528* (2013.01); *A61M 5/31551* (2013.01); *A61M 5/31555* (2013.01); *A61M 5/31585* (2013.01)

(58) Field of Classification Search
CPC .............. A61M 5/24; A61M 5/31525; A61M 5/31555; A61M 5/31528; A61M 5/3155; A61M 5/31551; A61M 5/31535; A61M 5/31585
USPC ................................................... 604/207, 211
See application file for complete search history.

(56) References Cited

U.S. PATENT DOCUMENTS

2004/0210199 A1* 10/2004 Atterbury et al. .............. 604/224
2007/0244436 A1* 10/2007 Saiki ............................. 604/131

FOREIGN PATENT DOCUMENTS

| WO | 02092153 A2 | 11/2002 |
| WO | 2006037434 A1 | 4/2006 |
| WO | 2010139632 A2 | 12/2010 |
| WO | 2011003762 A1 | 1/2011 |

* cited by examiner

*Primary Examiner* — Jason Flick
*Assistant Examiner* — Anh Bui
(74) *Attorney, Agent, or Firm* — McDonnell Boehnen Hulbert & Berghoff LLP

(57) ABSTRACT

A dose setting mechanism for a drug delivery device is provided comprising a dose setting member, a drive member, a clutch, a first clicker and second clicker. The first clutch and a second clutch are designed and adapted to each other such that at any time during operation either the first clutch rotationally couples the dose setting member and the drive member and/or the second clutch rotationally couples the drive member and the first clicker component. Further, the invention refers to an injection device with such a dose setting mechanism.

15 Claims, 2 Drawing Sheets

DOSE SETTING MECHANISM AND INJECTION DEVICE

CROSS REFERENCE TO RELATED APPLICATIONS

The present application is a U.S. National Phase Application pursuant to 35 U.S.C. §371 of International Application No. PCT/EP2012/055054 filed Mar. 22, 2012, which claims priority to European Patent Application No. 11159756.3 filed Mar. 25, 2011. The entire disclosure contents of these applications are herewith incorporated by reference into the present application.

FIELD OF INVENTION

The present invention is directed to a dose setting mechanism for a drug delivery device, like a pen-type injector, that provides for administration by injection of medicinal products from a multidose cartridge. The dose setting mechanism may comprise a housing, a dose setting member (number sleeve), a drive member (drive sleeve), a clutch and a clicker. Further, the invention refers to an injection device with such a dose setting mechanism.

BACKGROUND

In injection devices where the drive sleeve is coupled to the number sleeve via a clutch during dialing (dose setting) and coupled to the housing during dispense, via a clicker, and where coupling and decoupling is accomplished by a movement of the clutch member between a dialing (dose setting) and dispense position, it is important to ensure that in both general and misuse scenarios at extremes of tolerance, the user cannot decouple the drive sleeve from the number sleeve without first ensuring that it is sufficiently coupled to the housing.

If at any point the drive sleeve is neither coupled to the number sleeve nor to the housing with adequate strength, it may be possible for the user to rotate the drive sleeve relative to the number sleeve and housing. In devices where the drive sleeve has a threaded connection or splined connection to a piston rod that moves axially to expel the drug contents in the cartridge, rotating the drive sleeve relative to both the number sleeve and housing allows the user to back off the piston rod from the cartridge bung without decrementing the dialed dose, and this may lead to a severe under dose on the subsequent dose. If the drive sleeve is rotated in the opposite sense, it may also allow the user to expel drug without decrementing the dialed dose, leading to loss of drug and possible confusion.

FIG. 1 shows a known dose setting mechanism 1 where a spring 7 biases the clicker 6 into engagement with the clutch 5 and the clutch 5 into engagement with the number sleeve 3. Clicker teeth 6a, 6b of axial height 'Y1' engage between the clicker 6 and clutch 5 components and the clutch teeth 5a, 5b of axial height 'Z1' engage between the clutch 5 and the number sleeve 3 components. In this 'At rest' state a gap of 'X1' exists which is defined as the amount that the clicker 5 can move axially towards the drive sleeve 4 before the spring 7 is compressed to a solid state and prevents further axial movement.

This gap 'X1' has a total tolerance of 'T' which is made up from the addition of the individual tolerances of the component parts, clicker axial length, clutch axial length, number sleeve flange thickness, drive sleeve axial length and the spring height when compressed solid.

For the device to be dialable, the gap 'X1' in its minimum tolerance condition, X1-T, must still be large enough to allow the clicker teeth 6a, 6b to ride over each other during dialing so that the clutch 5 and hence drive sleeve 4 can rotate relative to the number sleeve 3. Hence the device must comply with the equation $$X1-T>Y1.$$

Similarly in order for the device to be able to dispense the gap X must be large enough to allow the clutch teeth 5a, 5b between the clutch 5 and number sleeve 3 to disengage. In this case, the device must comply with the equation $$X1-T>Z1.$$

In addition, to ensure that the drive sleeve 4 is either rotationally coupled via the clutch 5 to the number sleeve 3 or rotationally coupled to the housing 2 via the clutch 5 and clicker 6, and is not in some indeterminate state where it can rotate relative to both parts, the device must comply with the equation $$X1+T<Z1+Y1-K$$

where K is defined as the minimum overlap between either the clicker teeth 6a, 6b or the clutch teeth 5a, 5b to ensure that the drive sleeve 4 has sufficient engagement with one of these sets of teeth so as not to rotate relative to both sets. This minimum overlap K will have to be larger if the device is to be able to withstand rotation of the drive sleeve 4 relative to the housing 2 and the number sleeve 3 under a reasonable user applied torque. Adding the tolerance T to X1 allows to define a worst case combination of parts for this failure mode.

Combining the above three equations, $$X1-T>Z1 \quad (1)$$

$$X1-T>Y1 \quad (2)$$

and $$X1+T<Z1+Y1-K \quad (3)$$

one can substitute from (1) X1=Z1+T into (3) to give $$Y1>2*T+K$$

and from (2) one can substitute X1=Y1+T into (3) to give $$Z1>2*T+K.$$

Due to the long tolerance chain identified above this total stack tolerance of T may be as much as T=0.4 mm, and to ensure adequate strength K=0.4 mm as well. In this case Y1 must be greater than 2*0.4 mm+0.4 mm=1.2 mm. The clicker teeth 6a, 6b however have e.g. 24 positions per turn and hence 24 teeth. A height of 1.2 mm would require the clicker teeth to have a very steep flank angle given the restricted diameter of the part, and this flank angle would either make dialing not possible or give a very high dialing torque. In prototypes tested the clicker teeth height was only 0.7 mm and this gave a reasonable dialing torque.

WO 2006/037434 A1 discloses a drive mechanism for a drug delivery device. The embodiment of FIGS. 2 to 6 of this document includes a first clutch between a dose setting dial and an inner cylinder and a second clutch between the inner cylinder and a release knob. However, WO 2006/037434 A1 does not teach that at any time during operation either the first clutch couples the dose setting member a the drive member and/or the second clutch couples a drive member to a clicker component. Moreover, a clicker producing a tactile and/or audible feedback is not described in this document. In addition, in the mechanism of WO 2006/037434 A1 there is no clutch member located between the dose setting member to a drive member which clutch member is movable relative to these components in an axial direction.

SUMMARY

It is therefore an object of this invention to provide an improved and yet compact dose setting mechanism with a clicker system that decreases the risk of malfunction. In more detail, it is an object of the present invention to provide an alternative design of a clicker which does not have the restriction of X1−T>Y1.

This is obtained by a dose setting mechanism as defined in claim 1. A dose setting mechanism according to the present invention comprises a dose setting member, a drive member and a clutch member providing a first clutch located between the dose setting member and the drive member. The clutch member is preferably axially movable relative to the dose setting member and the drive member in order that the first clutch might rotationally couple or de-couple the dose setting member and the drive member. The dose setting mechanism further comprises a clicker having a first clicker component and a second clicker component. The first clicker is rotationally fixed to the housing in all permitted axial positions. The second clicker is rotationally fixed to the drive member in all permitted axial positions. The first and second clickers are axially movable relative to each other and to the drive member for producing a tactile and/or audible feedback during dialing, i.e. during relative rotational movement between the dose setting member and the housing. In addition, a second clutch is provided for rotationally coupling and de-coupling the drive member and the first clicker component. According to the present invention the first clutch and the second clutch are designed and adapted to each other such that at any time during operation either the first clutch rotationally couples the dose setting member and the drive member or the second clutch rotationally couples the drive member and the first clicker component or the first clutch rotationally couples the dose setting member and the drive member and the second clutch rotationally couples the drive member and the first clicker component. In other words, there is no point where both the first clutch rotationally decouples the dose setting member from the drive member and the second clutch rotationally decouples the drive member from the first clicker component simultaneously.

Typically, the axial movement of the clutch member for de-coupling the first clutch couples the second clutch and the axial movement of the clutch member de-coupling the second clutch couples the first clutch. According to the present invention the axial movement of the clutch member and the points of engagement/disengagement of the two clutches are adapted to each other such that the first clutch couples the dose setting member and the drive member prior to the second clutch de-coupling the drive member from the first clicker component. In a similar manner the second clutch couples the drive member and the first clicker component prior to the first clutch de-coupling the dose setting member and the drive member. This ensures that at all times during operation of the dose setting mechanism the drive member is either coupled to the dose setting member and/or to the first clicker component. Hence, the drive member is not allowed to rotate independent of either the dose setting member or the first clicker component.

The present invention is not limited to the above-mentioned embodiment. Different ways are possible to ensure that at any time during operation the drive member is either rotationally coupled to the dose setting member or to the housing (via the first clicker component). As an alternative to the above-mentioned embodiment, a blocking mechanism may be provided which blocks (prevents) de-coupling of either clutch as long as the other clutch is not in its coupled state.

Further, the present invention is not limited to embodiments where axial movement of the clutch member couples and de-couples the clutches. As an alternative, a different and/or additional component of the dose setting mechanism may be used to couple and de-couple the clutches. In this respect, it has to be assured, that at any time during operation either the first clutch rotationally couples the dose setting member and the drive member and/or the second clutch rotationally couples the drive member and the first clicker component. This may be achieved by a component part which entrains or diplaces, preferably the clutch member and/or the clicker, only if one of the two clutches is in its coupled state.

According to a preferred embodiment of the invention the coupling of the second clutch occurs as a result of the axial movement of the clutch member for rotationally de-coupling the first clutch between drive member and the dose setting member wherein the second clutch rotationally couples the drive member and the first clicker component prior to the first clutch rotationally de-coupling the dose setting member and the drive member. The coupling of the second clutch following the axial movement of the clutch member prior to de-coupling of the first clutch makes sure that the second clutch is actuated or moved to couple the drive member to the first clicker component before the first clutch de-couples the drive member from the dose setting member.

In a similar manner the coupling of the first clutch occurs as a result of the axial movement of the clutch member for rotationally de-coupling the second clutch between drive member and the first clicker component, wherein the first clutch rotationally couples the dose setting member and the drive member prior to the second clutch rotationally de-coupling the drive member and the first clicker component. Again, the coupling of the first clutch following the axial movement of the clutch member prior to de-coupling of the second clutch makes sure that the drive member is coupled to the dose setting member prior to being de-coupled from the first clicker component.

According to a preferred embodiment of the present invention the second clutch comprises first clutch teeth or splines provided on the drive member and corresponding second clutch teeth or splines provided on the first clicker component. In other words, the second clutch may either comprise separate components for coupling and de-coupling the drive member and the first clicker component or means for coupling or de-coupling the drive member and the first clicker component may be provided directly on the drive member and/or the first clicker component.

In addition, the first clutch preferably comprises first clutch teeth or splines provided on the dose setting member and corresponding second clutch teeth or splines provided on the clutch member. The clutch member could be a tubular element disposed on the drive member. Preferably, the tubular clutch member is interposed between the drive member and the dose setting member. Preferably, the clutch member is arranged such that it is rotationally coupled, but axially free, relative to the drive member, for example by means of splines along the length of the clutch member and drive member.

In a preferred arrangement of the dose setting mechanism according to the present invention the first clicker component is interposed between the clutch member of the first clutch and the second clicker component. The clutch member may have an end face abutting to a corresponding end face of the first clicker component.

According to a further development of this idea, the first clicker component preferably comprises first coupling teeth or splines and the clutch member of the first clutch comprises corresponding second coupling teeth or splines for rotationally coupling the first clicker component and the clutch member. The coupling teeth or splines may be provided as a series of shallow tooth profiles that engage between the clutch member and the first clicker component directly. Such shallow teeth serve to bias the clutch member towards one of a number of preferred rotational locations, for example aligning the clutch member, and hence the dose setting member, relative to the housing such that one of a given number of defined dose values can be selected. The shallow height of these teeth ensures minimal axial movement of the first clicker during dose dialing, when the second clutch, coupling first clicker and drive member, must not be engaged. Therefore, only a small movement of the clutch member is required in order to engage the second clutch. Thus, the design according to the present invention combines good dose number alignment and minimal dose button travel, which in turn minimizes the length of the pen.

It is preferred to have the first clicker component permanently rotationally coupled to a housing member and the second clicker component permanently rotationally coupled to the drive member. Thus, the two clicker components conduct a relative rotational movement if the drive member is rotated, e.g. during setting of a dose, to provide a angularly detented position for the dose setting member during dose dialing and to produce a tactile and audible feedback to the user as the dose setting member is turned. Further, the first clicker component being permanently rotationally coupled to a housing member allows coupling the drive member to the housing member via the first clicker component.

To produce a tactile and audible feedback to a user it is preferred to provide a clicker spring acting upon the first and second clicker components. Further, the clicker spring may bias the first clutch into its position coupling the dose setting member and the drive member.

According to preferred embodiment of the present invention, the dose setting member comprises a dose dial sleeve which is rotatable relative to the housing to set a dose. Further, the drive member may comprise a drive sleeve which is movable in a first axial direction relative to the housing member during dose setting and which is movable in a second axial direction relative to the housing member during dose dispensing, which second axial direction is opposite to said first axial direction. Preferably, the movement of the drive sleeve during dose setting includes a translational component and a rotational component, e.g. a movement along a helical path. During dose dispensing it is preferred that the drive sleeve moves only axially, i.e. without any rotational components of the movement.

If the first clutch rotationally couples the dose setting member and the drive member during dose setting and rotationally de-couples the dose setting member and the drive member during dose dispensing, the drive member follows a movement of the dose setting member along a helical path during dose setting while the dose setting member is allowed to rotate relative to the drive member during dose dispensing.

It is preferred if the first clicker component and the second clicker component are allowed to rotate relative to each other during dose setting and are rotationally locked together during dose dispensing.

Thus, the dose setting mechanism of the present invention provides an angular detent of the dose setting member for each dose division dialed, (giving both tactile and audible feedback), whilst ensuring that the drive sleeve is either coupled to the number sleeve or coupled to the housing at all times. The design of a two piece clicker ensures that the drive sleeve in a reusable injection device is coupled to either the number sleeve (during dialing) or to the housing (during dispense). This is to ensure that there is no mid position where the drive sleeve is free to rotate relative to the housing without incrementing or decrementing the displayed dose, for example during the transition between dialing and dispense or in case the user should, either deliberately or inadvertently, push on the dose button whilst simultaneously rotating the dose setting member.

The present invention is suitable for different types of injection devices. One example is a device similar to that shown in FIG. 2. This device may be either a disposable device, i.e. a device which has to be discarded after the cartridge containing a medicament is empty, or it may be a resettable device, i.e. a device having means allowing to replace an empty cartridge by a new one. In the latter case it is required to push back a spindle (piston rod) by either decoupling the spindle from the drive member or by allowing the drive member to spin relative to the dose setting member (e.g. a number sleeve). According to a preferred embodiment of the present invention, the drive member is a two-part component comprising a first driver part and a second driver part which may be rotationally coupled during dose setting and dose dispensing and which may be rotationally de-coupled during resetting. Preferably, a spring urges the two driver parts into engagement during dose setting and dose dispensing. This spring may be the clicker spring.

In addition or as an alternative to the above mentioned features, it is a basic idea of the present invention to provide a dose setting mechanism for a drug delivery device, the mechanism comprising: a dose setting member, a drive member, a clutch member located between the dose setting member and the drive member providing a first clutch for rotationally coupling and de-coupling the dose setting member and the drive member, a clicker comprising a first clicker component and a second clicker component axially movable relative to each other for producing a tactile and/or audible feedback during relative rotational movement there between and for rotationally coupling and de-coupling the drive member and the first clicker component, and further comprising a spring wherein the spring performs at least three of the following functions:

The spring biases in a resettable mechanism comprising a distal drive member part and a proximal drive member part the distal and proximal drive member parts into an engaged position (including re-engagement after reset).

The spring biases the first clicker component and the second clicker component together in order that they positively engage and deliver detented dialing positions and also the audible/tactile dialing click.

The spring biases the first clicker component and the clutch member (shallow biasing teeth) together in order that the clutch member and the first clicker component tend to rotate in such a way as to take up the slack between the various splines and grooves and therefore ensures good number alignment in the dose window.

In a resettable mechanism comprising a distal drive member part and a proximal drive member part, the spring provides a force during dose dispense that drives the distal (front) part of the drive member forwards, thus delivering the dose.

At the end of the dose the compressed spring provides the force required to complete the delivery of the dose.

The spring resists in a resettable mechanism decoupling of the distal and proximal drive member parts with a small force. Therefore, when resetting the spindle (piston rod) cannot 'fall back' into the device under gravity. This is a disadvantage of certain other resettable devices because if their cartridge holder becomes partially detached then reset of the spindle can occur without the user noticing, resulting in underdose on the next dose.

The spring biases the dose setting member (e.g. a dial sleeve) and teeth of the clutch member into engagement at the completion of the dose, thus ensuring that they are coupled during dialing of the subsequent dose.

According to a preferred embodiment, the spring is designed as a wave spring. In particular, the 'wave' spring design of spring has advantages over other, more conventional, coil springs. For example, the wave spring takes up less space when in its coil bound condition. This reduces the overall length of the device. Further, the force profile of the spring is non-linear. Thus the spring can apply a relatively low force for its initial compression (including when resetting the device) but the force will rise rapidly as the spring approaches its coil-bound state (e.g. under high dispense loads).

BRIEF DESCRIPTION OF THE DRAWINGS

In the following, the invention will be described by a way of an example and with reference to the schematic drawings in which.

DETAILED DESCRIPTION

Figure 1:
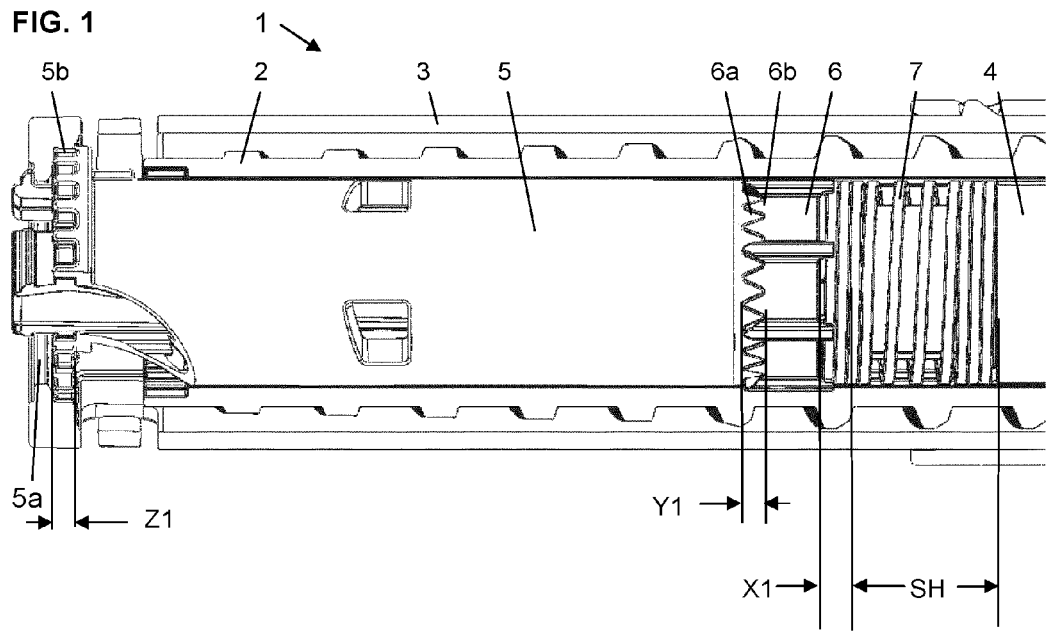
FIG. 1 shows a known dose setting mechanism.

FIG. 1 shows a typical dose setting mechanism 1 of an injection device with a clicker mechanism. The dose setting mechanism comprises an (internal) housing member 2, a dose setting member 3 comprising a number sleeve (dose dial sleeve) for displaying the set dose to the user, a drive member 4 in the form of a drive sleeve, a clutch member 5 and a clicker 6. The clutch member 5 is located between the dose setting member 3 and the drive member 4. The clutch member 5 is axially movable relative to the dose setting member 3 and the drive member 4 for rotationally coupling and de-coupling the dose setting member 3 and the drive member 4. As shown in FIG. 1, the first clutch 5 uses two sets of matching face teeth 5a, 5b which are provided on an inner end face of the dose setting member 3 and a corresponding end face of the tubular clutch member 5.

In a similar manner, the clicker mechanism uses two sets of matching face teeth 6a, 6b in conjunction with a coil spring 7 to provide the detents for the dialed dose and the clicks for tactile and audible feedback. In other words, teeth 6a, 6b, which are provided on tubular clutch member 5 and a clicker member 6 respectively, will tend to rest in an engaged position and are allowed to ride one over the other during dose setting.

In the dose setting mechanism shown in FIG. 1, clicker member 6 is keyed to the housing member 2 by means of longitudinally directed splines to prevent relative rotation between the clicker member 6 and the housing member 2, while allowing relative axial movement there between. In a similar manner, clutch member 5 is keyed to the drive member 4 by means of longitudinally directed splines to prevent relative rotation between the clutch member 5 and the drive member 4, while allowing relative axial movement there between.

The spring 7 serves to provide the necessary axial force to engage clutch teeth 5a on clutch component 5 (which is splined to the drive sleeve 4) with clutch features 5b on the number sleeve 3 at the end of a delivered dose and during subsequent dialing of the next dose. Further, the spring provides the axial force between the clutch component 5 and clicker component 6 that causes the matching face teeth 6a, 6b to click during dialing. In this way the one spring 7 serves two functions.

FIG. 1 shows the device with a dose button (not shown) depressed. This causes axial movement of the clutch member in the direction which decouples the clutch teeth 5a, 5b between the clutch member 5 and the number sleeve 3 and compresses the clicker spring 7. Whether or not the clicker spring 7 is compressed to a solid state, the axial force provided by this spring is sufficient to prevent the clicker face teeth 6a, 6b from disengaging under any dispense loads applied by the user to the button during dispense. These clicker face teeth 6a, 6b therefore rotationally lock the clicker 6 to the clutch member 5 and as the clicker 6 is splined to the housing member 2 and the clutch member 5 is splined to the drive sleeve 4, this effectively locks the drive sleeve 4 to the housing member 2 in rotation.

However in order to allow for dialing, the clicker 6 must be free to rotate relative to the drive sleeve 4 when the dose button is not depressed. This causes a problem in the device which is highlighted in FIG. 1. Here the user has pushed the dose button in, decoupling the clutch teeth 5a, 5b between the clutch member 5 and number sleeve 3, and has then rotated the dose button. The dose button is splined to both the clutch member 5 and drive sleeve 4 and in some tolerance conditions a user may be able to rotate the dose button and hence drive sleeve 4 and clutch member 5 bumping over the clicker teeth 6a, 6b without the clutch teeth 5a, 5b between the clutch member 5 and number sleeve 3 re-engaging, this enabling the drive sleeve 4 to be rotated relative to the number sleeve 3. A similar problem can occur even at nominal tolerances if the user applies rotational torque to the dose button whilst the dose button is held in a partially depressed condition. In this condition both the clutch teeth 5a, 5b and clicker teeth 6a, 6b would be only minimally engaged, e.g. at the tips of both sets of teeth. Should the user continue to apply further rotational torque then these teeth can deform either elastically or plastically and permit rotational movement of the drive sleeve 4 relative to the number sleeve 3. Once plastic deformation of the teeth has occurred then the rotational strength of the couplings is significantly reduced, making subsequent failures more likely to occur.

Such failures are most likely to occur when the number sleeve 3 is dialed either to the minimum or maximum dose (e.g. 80 units stop). At the maximum dose the device of FIG. 1 has maximum dose rotational stop features between the number sleeve 3 and the outer housing (not shown). By pressing the dose button, the user is able to decouple the number sleeve 3 from the drive sleeve 4, effectively bypassing this stop and then continue to rotate the button and hence drive sleeve 4, thus dispensing some drug.

Alternatively if the dose button is rotated at the minimum dose rotational stop (0 units stop) so as to dial down, the number sleeve 3 is prevented from rotation and rotation of the drive sleeve 4 in this case will cause the piston rod (not shown) to be wound back into the drive sleeve 4, and 'back off' the piston rod from the cartridge bung, opening a gap between the piston rod and the cartridge bung. This gap may not be obvious to the user and, if not corrected by the user performing a priming step to check for correct operation, would result in an underdose on any subsequent dialed dose, as the piston rod would first have to advance to close the gap before any drug is dispensed, reducing the volume of drug dispensed.

The axial displacement of clicker 6 during dose dialing is equal to the height of the clicker teeth 6a, 6b (approximately 0.7 mm plus and minus a tolerance). During the axial displacement, i.e. during dose dialing, the clicker 6 must be free to rotate relative to the drive sleeve 4. The rotational lock of the clicker 6 to the drive sleeve 4 during dispense, can therefore only occur after the clicker has moved axially by at least the 0.7 mm plus tolerance. As the clutch teeth 5a, 5b in the design of FIG. 1 decouple after only 0.8 mm plus tolerance, rotationally locking the clicker 6 to the drive sleeve 4 before the clutch teeth 5a, 5b disengage in all tolerance conditions is not possible. Even at nominal dimensions the clicker teeth 6a, 6b are only minimally engaged (by a maximum of 0.1 mm) at the point where the clutch teeth 5a, 5b disengage. Increasing the 'overlap', e.g. by lengthening the engagement of clutch teeth 5a, 5b increases the overall length of the pen by at least double the amount of the increase (the mechanism inside the housing must accommodate the increased movement of the clutch member and the dose button to housing gap must also increase by the same amount to permit this movement). In addition this changes the dispensing characteristics of the pen—the user must now press the dose button further before dispensing will begin.

Figure 2:
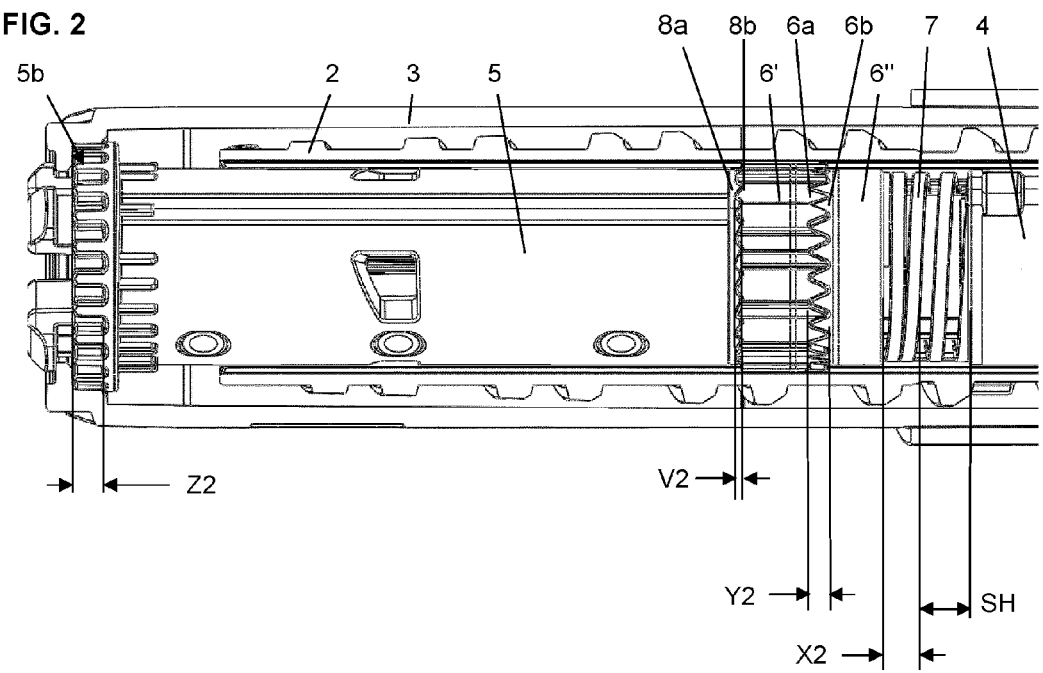
FIG. 2 shows a dose setting mechanism according to the invention.
Figure 3:
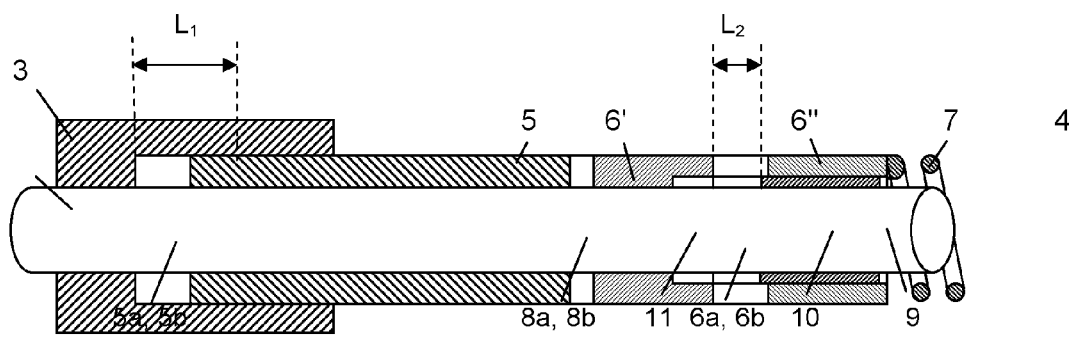
FIG. 3 shows an enlarged detail of a dose setting mechanism similar to that of FIG. 2.

A solution according to the present invention is shown in FIGS. 2 and 3 keeping the clutch axial engagement at 0.8 mm, the clicker teeth height at 0.7 mm but ensuring that the drive sleeve 4 is prevented from rotating relative to the clicker 6 before the clutch 5 has fully disengaged.

In FIG. 2, a dose setting mechanism is shown where the clicker is split into two parts, first clicker component 6' and second clicker component 6". The first clicker component 6' is similar to the clicker 6 in FIG. 1 in that it is splined to the housing member 2 and therefore must rotate relative to the drive sleeve 4 and clutch components 5 during dialing. However, the clicker teeth 6a, 6b have been moved from the end face that engages with the clutch member 5 to the opposite end face where they engage with the additional part, second clicker component 6". Hence, first clicker component 6' has very limited axial movement during dialing (only moving by the height of the shallow teeth 8a, 8b) and therefore it can be rotationally locked to the drive sleeve 4 after only a very small relative axial displacement, as shown in FIG. 3, and well within the axial engagement of the clutch teeth 5a, 5b.

The second clicker component 6" component is always rotationally coupled to the drive sleeve 4 and moves axially compressing the clicker spring 7 to overcome the clicker face teeth 6a, 6b during dialing.

This design solution requires an extra component, however it enables a lower button travel and steeper clicker teeth 6a, 6b (giving a stronger audible and tactile click), compared to the single clicker design shown in FIG. 1 for the reasons described above, and it also ensures that during dialing and dispense, the clicker spring 7 does not have to rotate relative to any other component. This second advantage ensures that the dialing tactile and audible feedback is improved, and will reduce wear on the faces that contact the metal clicker spring 7.

Figure 4:
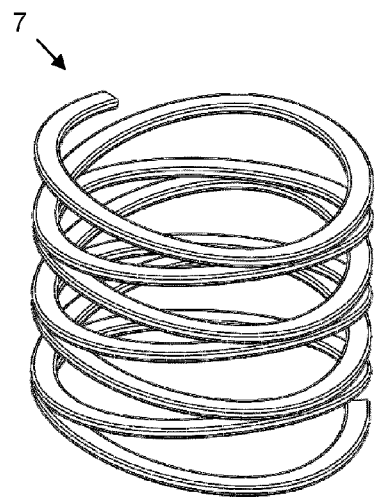
FIG. 4 shows a perspective view of the spring of the dose setting mechanism of FIG. 2, and FIG. 5 a detail of the inner surface of the clutch member of the dose setting mechanism of FIG. 2.

According to a preferred embodiment, spring 7 is a wave spring as depicted in FIG. 4. The wave spring 7 may comprise a series of curved or dished elastically deformable washers (perforated disks) which are arranged conversely, i.e. the curvature of adjacent washers is contrariwise such that adjacent washers contact each other (or may be fixed to each other) in two points and are spaced from each other for the rest. Thus, the wave spring takes up less space when in its coil bound condition. A further advantage is that the force profile of wave spring 7 is non-linear.

It is preferred to avoid that the rotational coupling between the clutch member 5 and hence number sleeve 3 relative to the first clicker component 6' and hence housing member 2 has to pass via two additional interfaces compared to FIG. 1 because this would increase the chain of tolerances between the housing member 2 and the number sleeve 3 and therefore lead to poor alignment of the displayed dose number relative to the housing member 2. Assuming the absence of shallow teeth features 8a, 8b, then the first additional interface would be from the second clicker component 6" to the drive sleeve 4 and the second additional interface would be the splined connection between the clutch member 5 and the drive sleeve 4. These two additional interfaces would result in more play and misalignment between the numbers displayed on the number sleeve 3 and the dose number window aperture on the housing member 2 which can make the reading of the dialed dose confusing for the user. To avoid the above drawback, a series of shallow tooth profiles 8a, 8b is added that engage between the clutch member 5 and the first clicker component 6' directly, similar to the clicker teeth shown in FIG. 1, but much smaller in height. These shallow teeth 8a, 8b are shown in FIG. 3 and serve to rotationally bias the clutch component 5, within the angular limits provided by the play in the rotational interfaces between second clicker 6" to drive sleeve 4 and drive sleeve 4 to clutch member 5, towards one of a number of preferred rotational positions, thus combining a good dose number alignment, with the robustness and minimal button travel of the present invention.

FIG. 3 shows in more detail how the second clicker component 6" component is keyed to the drive member 4 to prevent relative rotation between the the second clicker component 6" and the drive member 4, while allowing relative axial movement there between during dose setting. The drive sleeve 4 is provided with at least one longitudinally directed spline 10 (protrusion) located on the outer face of the drive member 4. The second clicker component 6" has at least one corresponding groove 9 for receiving spline 10. The length of spline 10 is designed to be long enough to guide the second clicker component 6" and to prevent relative rotation between the second clicker component 6" and the drive member 4 even if the second clicker component 6" moves relative to the drive member 4 in its axial direction whilst riding over the clicker teeth of the first clicker component 6' during dialing.

In a similar manner, the first clicker component 6' is provided with a groove 11 for receiving spline 10 if the clutch member 5 and the first clicker component 6' are pushed to the right in FIG. 3 against the force of the clicker spring 7. Thus, spline 10 and groove 11 constitute a second clutch for coupling the drive sleeve 4 (via first clicker component 6') to the housing member 2.

As depicted in FIG. 3, the length $L_1$, the distance by which the clutch teeth 5a, 5b have to be axially displaced for decoupling the drive sleeve 4 from the number sleeve 3, is larger than the length $L_2$, the distance by which the first clicker 6' must be axially displaced before coupling the drive sleeve 4 to the first clicker 6'. Thus, spline 10 of the drive sleeve 4 will rotationally lock the first clicker component 6' by engaging groove 11 prior to de-coupling of the drive sleeve 4 from the number sleeve 3.

Regarding the equations mentioned above with respect to FIG. 1, the design shown in FIGS. 2 and 3 has the clicker split into two parts, with one part splined to the housing, clicker part 6', and the second part splined to the drive sleeve, clicker part 6". As mentioned above, in this arrangement a second clutch is introduced between clicker part 6' and the drive sleeve which does not engage during dialing, but does engage when the button is depressed and crucially engages before the clutch teeth between the clutch and number sleeve have disengaged for all tolerance conditions. Because this second clutch is independent to the clicker teeth it can be designed to engage soon after the button has been depressed. This second clutch cannot be seen in FIG. 2 but a schematic cross section of FIG. 2 is shown in FIG. 3, where it can be seen that this second clutch engages after the button has been depressed a distance $L_2$.

In addition the design in FIGS. 2 and 3 also has a second set of clicker teeth 8a, 8b between the clutch and clicker part 6'. This second set of clicker teeth have an axial height 'V2' and are present purely to ensure that at rest, these teeth engage to control the relative rotational position of the clutch relative to the clicker part 6' to ensure that the number sleeve (which is coupled to the clutch) has good number alignment with the dose window which is splined to the clicker part 6' via the housing.

Looking at the equations again this time using X2, Y2 and Z2 as before with in addition a further dimension 'V2' which is the axial tooth height of the second set of clicker teeth 8a, 8b between the clutch member 5 and the clicker part 6' the device must comply with the following equations $$X2-T>Y2+V2 \quad (1)$$

to enable the device to be dialed, $$L2-T2>V2 \quad (2)$$

again to enable the device to be dialed (where T2 is the tolerance on the stack that defines gap $L_2$), $$X2-T>Z2 \quad (3)$$

to enable the device to be dispensed and $$L2+T2<Z2+Y2-K \quad (4)$$

to ensure one of the clutches are always engaged by an amount greater than K.

If T2 is 0.2 mm (due to the shorter tolerance chain of parts) and V2 is 0.15 mm (just enough to give a detent position between the clutch member 5 and the clicker part 6') one gets from equation (2) L2>V2+T2, i.e. L2>0.35 mm.

A good value for Z2 is 1.2 mm and as already mentioned above a value of Y2=0.7 mm gives a good dialing torque. Inserting these values into equation (4), K<Z2+Y2−L2−T2, i.e. K<1.2+0.7−0.35−0.2 or K<1.35 mm. Note that equations (1) and (3) are also satisfied with these values above.

This means that the device can be designed to always have an overlap between the clutches of K=1.35 mm which will be enough to ensure that the user is unable to disengage the drive sleeve from both the housing and the number sleeve at the same time even if a high torque is applied to the plastic parts.

Clicker spring 7 may have a wave spring design. The clicker spring 7 is particularly advantageous in that it performs several functions. Preferably, spring 7 biases the first clicker component 6' and the second clicker component 6" together in order that they positively engage and deliver detented dialing positions and also the audible/tactile dialing click. In addition, the clicker spring 7 biases the first clicker component 6' and the clutch member 5 (shallow biasing teeth) together in order that the clutch member 5 and the first clicker component 6' tend to rotate in such a way as to take up the slack between the various splines and grooves and therefore ensures good number alignment in the dose window. Further, the clicker spring 7 biases the dose setting member 1 (e.g. a dial sleeve) and teeth of the clutch member 5 into engagement at the completion of the dose, thus ensuring that they are coupled during dialing of the subsequent dose.

In FIGS. 2 and 3, the drive member 4 (drive sleeve) is not depicted in detail. The drive member may be a single part or may alternatively comprise two drive member parts. The latter is especially preferred if the dose setting mechanism is a resettable mechanism allowing to replace a cartridge containing a medicament. In this case, the clicker spring 7 may perform additional function. The clicker spring 7 preferably biases the distal and proximal drive member parts into an engaged position (including re-engagement after reset). In addition, the clicker spring 7 may provide a force during dose dispense that drives the distal (front) part of the drive member forwards, thus delivering the dose. At the end of the dose the compressed spring provides the force required to complete the delivery of the dose. The spring may further resists decoupling of the distal and proximal drive member parts with a small force. Therefore, when resetting the spindle (piston rod) cannot 'fall back' into the device under gravity. This is a disadvantage of certain other resettable devices because if their cartridge holder becomes partially detached then reset of the spindle can occur without the user noticing, resulting in underdose on the next dose.

There are different embodiments ensuring that at any time during operation either the first clutch 5a, 5b rotationally couples the dose setting member 3 and the drive member 4 and/or the second clutch 9, 11 rotationally couples the drive member 4 and the first clicker component 6' as depicted in FIGS. 2 and 3:

According to a first embodiment both clutch member 5 and first clicker component 6' move together axially as one component when the button (not shown) is depressed/released to engage and disengage the two clutches with the clutch between the first clicker component 6' and drive sleeve 4 engaging before the clutch between the clutch member 5 and dose setting member 3.

According to a second embodiment, when the clutch member 5 starts to move axially the first clicker component 6' also starts to move axially and when the clutch member 5 stops moving the first clicker component 6' stops moving. I.e. they are coupled but the axial distance that each part travels is not necessarily the same. If for instance the two parts engage each other with helical ramps, and for instance the clutch member 5 rotates relative to the first clicker component 6' during this axial travel then some relative axial movement will occur between the two components and they will not move axially by exactly the same distance. This is what happens in the device depicted in FIG. 2 as the first coupling teeth or splines 8a are helical ramps between the clutch member 5 and first clicker component 6' if there is a step in the groove in the clutch member 5 which engages a spline of the drive member 4 which causes the clutch member 5 to rotate relative to the first clicker component 6' when the clutch member 5 is moved axially.

Figure 5:
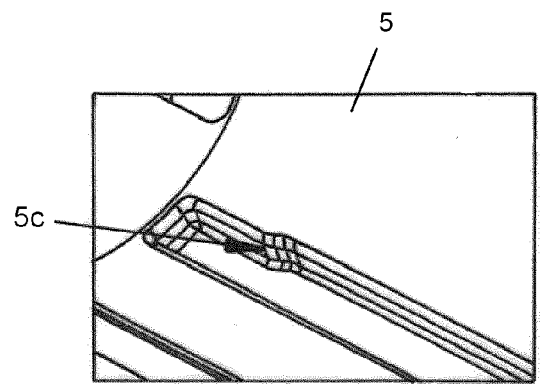

Such a feature is shown in FIG. 5 depicting a detail of the inner surface of clutch member 5 which is keyed to drive member 4 by means of longitudinally directed splines formed on the drive member 4 outer surface which engage corresponding grooves of the clutch member 5 to prevent relative rotation between the clutch member 5 and the drive member 4, while allowing relative longitudinal movement there between. In each groove there is a step 5c which prevents proximal movement of the drive member 4 during normal reset. In other words, said grooves have a distal portion of larger width and a proximal portion of smaller width with the step 5c located at the transition between these two portions. Thus, depending on the axial arrangement of the spline within the groove proximal movement of the spline is either stopped by step 5c or allowed guiding the spline in the portion of the groove with the smaller width. As an alternative the spline(s) may be provided on the clutch member and the groove(s) may be provided on the drive member.

A third embodiment could be where there is a delay between the axial travel of the first clicker component 6' and axial travel of the clutch member 5 so that it is ensured that the first clicker component 6' has moved axially to lock the first clicker component 6' in rotation to the drive member 4 before the clutch between the clutch member 5 and dose setting member 3 starts to disengage. This could be achieved by either acting on the first clicker component 6' to move it axially and then after a pre-defined movement this part entrains the clutch member 5 so that they then move together. Or as an alternative, the clutch member 5 could be split into two parts, a part that acts on the first clicker component 6' and second part that is rotationally coupled to the first part that also forms the clutch to the dose setting member 3. These two parts are sprung apart with a spring force that is weaker than the main clutch spring 7 so that when the first clutch part is moved axially it acts on the first clicker component 6' but the second part of the clutch remains fully engaged with the dose setting member 3. Only after a predefined displacement of the first part of the clutch member 5 does it entrain the second part of the clutch so as to disengage this from the dose setting member 3.

The dose setting mechanism may be part of an injection device further comprising a cartridge containing a medicament. The cartridge may be held in a cartridge holder which can be permanently or releasably attached to the dose setting mechanism.

The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(0)14, Asp28] Exendin-4(1-39),
des Pro36 [Met(0)14, IsoAsp28] Exendin-4(1-39),
des Pro36 [Trp(02)25, Asp28] Exendin-4(1-39),
des Pro36 [Trp(02)25, IsoAsp28] Exendin-4(1-39),
des Pro36 [Met(0)14 Trp(02)25, Asp28] Exendin-4(1-39),
des Pro36 [Met(0)14 Trp(02)25, IsoAsp28] Exendin-4(1-39); or
des Pro36 [Asp28] Exendin-4(1-39),
des Pro36 [IsoAsp28] Exendin-4(1-39),
des Pro36 [Met(0)14, Asp28] Exendin-4(1-39),
des Pro36 [Met(0)14, IsoAsp28] Exendin-4(1-39),
des Pro36 [Trp(02)25, Asp28] Exendin-4(1-39),
des Pro36 [Trp(02)25, IsoAsp28] Exendin-4(1-39),
des Pro36 [Met(0)14 Trp(02)25, Asp28] Exendin-4(1-39),
des Pro36 [Met(0)14 Trp(02)25, IsoAsp28] Exendin-4(1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2, H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4 (1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDahttp://en.wikipedia.org/wiki/Dalton_%28unit%29) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. A dose setting mechanism for a drug delivery device, the mechanism comprising:
   a dose setting member,
   a drive member,
   a clutch member located between the dose setting member and the drive member, the clutch member being axially movable relative to the dose setting member and to the drive member and being rotationally fixed to the drive member, providing a first clutch for rotationally coupling and de-coupling the dose setting member and the drive member,
   a clicker comprising a first clicker component and a second clicker component axially movable relative to each other for producing a tactile and/or audible feedback during dose setting of the drug delivery device,
   wherein the first clicker component is axially movable relative to the drive member providing a second clutch for rotationally coupling and de-coupling the drive member and the first clicker component,
   wherein the first clutch and the second clutch are designed and adapted to each other such that at any time during operation either the first clutch rotationally couples the dose setting member and the drive member and/or the second clutch rotationally couples the drive member and the first clicker component.

2. The dose setting mechanism according to claim 1, characterized in that the first clicker follows the axial movement of the clutch member during the axial movement of the clutch member for rotationally de-coupling the first clutch between drive member and the dose setting member, wherein the second clutch rotationally couples the drive member and the first clicker component prior to the first clutch rotationally de-coupling the dose setting member and the drive member.

3. The dose setting mechanism according to claim 1, characterized in that the clutch member follows the axial movement of the first clicker during the axial movement of the first clicker for rotationally de-coupling the drive member and the first clicker component, wherein the first clutch rotationally couples the dose setting member and the drive member prior to the second clutch rotationally de-coupling the drive member and the first clicker component.

4. The dose setting mechanism according to claim 1, characterized in that the second clutch comprises first clutch teeth or splines provided on the drive member and corresponding second clutch teeth or splines provided on the first clicker component.

5. The dose setting mechanism according to claim 1, characterized in that the first clutch comprises first clutch teeth or splines provided on the dose setting member and corresponding second clutch teeth or splines provided on the clutch member.

6. The dose setting mechanism according to claim 5, characterized in that the first clicker component is interposed between the clutch member of the first clutch and the second clicker component.

7. The dose setting mechanism according to claim 5, characterized in that the first clicker component comprises first coupling teeth or splines and the clutch member comprises corresponding second coupling teeth or splines for rotationally aligning the first clicker component and the clutch member.

8. The dose setting mechanism according to claim 1 further comprising a housing member, characterized in that the first clicker component is permanently rotationally coupled to the housing member and the second clicker component is permanently rotationally coupled to the drive member.

9. The dose setting mechanism according to claim 1, characterized in that a clicker spring is provided acting upon the second clicker component.

10. The dose setting mechanism according to claim 1, characterized in that the dose setting member comprises a dose dial sleeve or number sleeve which is rotatable relative to a housing member to set a dose, and that the drive member comprises a drive sleeve which is movable in a first axial direction relative to the housing member during dose setting, and which is movable in a second axial direction relative to the housing member during dose dispensing, which second axial direction is opposite to said first axial direction.

11. The dose setting mechanism according to claim 1, characterized in that the clutch member rotationally couples the dose setting member and the drive member during dose setting and rotationally de-couples the dose setting member and the drive member during dose dispensing.

12. The dose setting mechanism according to claim 1, characterized in that the first clicker component and the second clicker component are allowed to rotate relative to each other during dose setting and are rotationally locked together during dose dispensing.

13. The dose setting mechanism according to claim 1, characterized in that the second clicker component free to move axially relative to the drive member but is rotationally locked to the drive member.

14. The dose setting mechanism according to claim 1, further comprising
   a clicker spring which
      biases the first clicker component and the second clicker component together,
      biases the first clicker component and the clutch member together,
      biases the dose setting member and the clutch member into engagement,
      biases two parts of the drive member, which comprises a distal and proximal drive member part, into an engaged position,
      provide a force during dose dispense that drives the distal (front) part of the drive member forwards, and/or
      resists decoupling of the distal and proximal drive member parts with a force in the magnitude order of gravity.

15. Injection device comprising the dose setting mechanism of claim 1 and a cartridge containing a medicament.

* * * * *